United States Patent
Schroeder (10) Patent No.: US 7,521,586 B2
(45) Date of Patent: Apr. 21, 2009

(54) PACKAGING FOR ADHESIVE-SIDED ARTICLES TO ALLOW ONE-HANDED APPLICATION

(75) Inventor: Mark R. Schroeder, Houston, TX (US)

(73) Assignee: Aso, LLC, Sarasota, FL (US)

( * ) Notice: Subject to any disclaimer, the term of this patent is extended or adjusted under 35 U.S.C. 154(b) by 677 days.

(21) Appl. No.: 09/819,040

(22) Filed: Apr. 23, 2001

(65) Prior Publication Data

US 2002/0064619 A1    May 30, 2002

Related U.S. Application Data

(62) Division of application No. 09/589,386, filed on Jun. 7, 2000, now Pat. No. 6,225,522, which is a division of application No. 09/206,885, filed on Dec. 8, 1998, now Pat. No. 6,124,522.

(60) Provisional application No. 60/109,701, filed on Nov. 24, 1998.

(51) Int. Cl.
*A61F 13/00* (2006.01)

(52) U.S. Cl. .............. 602/57; 602/41; 602/42; 602/43; 602/52; 602/54; 206/441

(58) Field of Classification Search ............ 602/41–59, 602/900, 909; 206/440, 441, 436, 369; 609/180; 24/159; 221/25, 33, 76; 128/888, 889

See application file for complete search history.

(56) References Cited

U.S. PATENT DOCUMENTS

| | | | |
|---|---|---|---|
| 2,465,876 A | 3/1949 | Hornung | 206/16 |
| 2,587,928 A | 3/1952 | Tuck et al. | 312/39 |
| 2,627,341 A | 2/1953 | Morgan | 206/63.2 |
| 2,887,247 A | 5/1959 | William, Jr. | 221/25 |

(Continued)

FOREIGN PATENT DOCUMENTS

EP    0051935    5/1982

(Continued)

OTHER PUBLICATIONS

"Bertek Pouch/patch Applicator Wound Dressing Machine", BERTEK Brochure, 1991.

(Continued)

*Primary Examiner*—Kim M Lewis
(74) *Attorney, Agent, or Firm*—Gray Robinson, P.A.

(57) ABSTRACT

A packaged article including an adhesive-sided article, such as an adhesive bandage, and packaging formed of top and bottom backing sheets with a release layer disposed either directly on the bottom backing sheet facing the adhesive side of the article or on release paper carried on the bottom backing sheet. The facing surfaces of the top backing sheet and bottom backing sheet peripherally surrounding the adhesive-sided article have cohesive surfaces. An adhesive strip, preferably a double-sided adhesive strip, attaches the non-adhesive side of the adhesive-sided article to the top backing sheet. The top sheet is used as an applicator for placing the article onto a target surface, such as a patient's skin. The cohesive surface of the top sheet surrounding the article does not adhere to the target surface. A release layer applied directly on the bottom backing sheet eliminates additional material and waste.

38 Claims, 4 Drawing Sheets

U.S. PATENT DOCUMENTS

| | | | | |
|---|---|---|---|---|
| 2,969,145 A | 1/1961 | Hannauer, Jr. | | 206/63.2 |
| 3,313,405 A | 4/1967 | Blackford | | 206/63.2 |
| 3,520,403 A | 7/1970 | Moshel | | 206/63.2 |
| 3,530,494 A | 9/1970 | Baratta | | 206/63.2 |
| 3,630,346 A | 12/1971 | Burnside | | 206/42 |
| 3,809,221 A | 5/1974 | Compere | | 206/461 |
| 3,835,992 A | 9/1974 | Adams, IV | | 206/390 |
| 3,899,077 A | 8/1975 | Spiegelberg | | 206/441 |
| 4,182,449 A | 1/1980 | Kozlow | | 206/441 |
| 4,194,624 A | 3/1980 | Spiegelberg | | 206/441 |
| 4,265,234 A | 5/1981 | Schaar | | 128/156 |
| 4,336,097 A | 6/1982 | Van Kampen et al. | | 156/527 |
| 4,499,896 A | 2/1985 | Heinecke | | 128/156 |
| RE32,010 E | 10/1985 | Collins | | 156/527 |
| 4,600,001 A | 7/1986 | Gilman | | 128/156 |
| 4,666,040 A | 5/1987 | Murata | | 206/441 |
| 4,759,652 A | 7/1988 | Ulrich | | 401/196 |
| 4,787,380 A | 11/1988 | Scott | | 128/156 |
| 4,807,753 A | 2/1989 | Goldstein | | 206/390 |
| 4,915,102 A | 4/1990 | Kwiatek et al. | | 128/156 |
| 4,993,586 A | 2/1991 | Taulbee et al. | | 221/25 |
| RE33,727 E | 10/1991 | Sims | | 128/85 |
| 5,102,008 A | 4/1992 | Kaufman et al. | | 221/25 |
| 5,133,477 A | 7/1992 | Etheridge et al. | | 221/25 |
| 5,160,315 A | 11/1992 | Heinecke et al. | | 602/57 |
| 5,242,725 A | 9/1993 | Weissmann et al. | | 428/40 |
| 5,511,689 A | 4/1996 | Frank | | 221/73 |
| 5,685,833 A | 11/1997 | Turngren | | 602/58 |
| 5,722,943 A | 3/1998 | Sessions | | 602/57 |
| 6,124,522 A * | 9/2000 | Schroeder | | 602/57 |

FOREIGN PATENT DOCUMENTS

| | | |
|---|---|---|
| EP | 0066899 | 12/1982 |
| EP | 008199 | 5/1983 |
| EP | 4314834 | 10/1994 |
| FR | 1002738 | 3/1952 |
| GB | 2120104 | 11/1983 |
| GB | 2157955 | 11/1985 |
| JP | 59214449 | 4/1984 |
| JP | 2126815 | 7/1996 |
| US | 9838955 | 9/1998 |
| WO | 8911262 | 11/1989 |

OTHER PUBLICATIONS

"Tegaderm Transparent Dressing", 3M HealthCare Brochure, Oct. 1991.

* cited by examiner

PACKAGING FOR ADHESIVE-SIDED ARTICLES TO ALLOW ONE-HANDED APPLICATION

This Application claims the benefit of U.S. Provisional Application No. 60/109,701, filed Nov. 24, 1998.

BACKGROUND OF THE INVENTION

1. Field of the Invention

The invention relates to the packaging and application of adhesive-sided articles such as adhesive bandages, medical tapes, and the like.

2. Description of the Prior Art

Individually packaged adhesive-sided articles have been in use for many decades. Of these, perhaps the best known example is the adhesive bandage such as the one marketed by Johnson & Johnson under the famous BAND-AID® trademark. The packaging of this product and many others like it consists of an outer envelope or sleeve that must be opened to extract the product, as well as one or more pieces of release material that must be removed from the product itself to expose the adhesive. However, a significant difficulty arises in using such products in situations where the user does not have both hands free to unwrap and apply the bandage. For example, a worker who suffers a serious cut on one finger or hand would find it virtually impossible to apply a standard adhesive bandage quickly because he would have to use both hands to unwrap the bandage but could not possibly use both to apply it. Similarly, a person who must inject himself (or someone else) with medication or draw a blood sample would doubtless prefer to hold a gauze pad against the puncture with one hand while applying a bandage or adhesive tape over the gauze. The difficulty of application is aggravated where the bandages are stored in a cardboard or metal box or other closed receptacle, for an injured user might contaminate multiple wrapped bandages while attempting to extract one from the receptacle. In view of the well-documented frequency of hand and finger injuries in both the home and workplace, there is clearly a need for adhesive bandages that the user can obtain, unwrap and apply quickly while using only one hand.

Matters are further complicated for health care professionals, who are subject to OSHA requirements that mandate the use of latex gloves during all activities which involve a risk of exposure to blood. Traditional adhesive bandages adhere tenaciously to latex, making it difficult to apply them using two gloved hands, much less with only one.

At the same time, however, it is essential for achieving a complete solution to the problem that the bandage also be maintained in a sterile condition until just before application. Furthermore, the benefit of such precautions is wasted if the user is forced for some reason to touch the sterile dressing while applying the bandage. Typically this occurs while the user is shifting his grip on the bandage, just after unwrapping it but before applying it.

Many solutions have been put forth to address the problems described above. Most solutions have relied on the use of some complex (and expensive) dispensing apparatus that presents a single sterile bandage from the end of a fanfold stack or coiled roll. Some of these also achieve the goal of single-handed application, but these solutions are often especially expensive and cumbersome. Furthermore, most of the solutions that accomplish one-handed application do so by methods that leave a substantial portion of the article secured to its wrapper during application, such as shown in U.S. Pat. No. 4,265,234, Schaar. This attachment makes it difficult to apply the article to cylindrical surfaces (e.g., bandaging a finger) without wrapping the article's adhesive layer back over part of the wrapper.

U.S. Pat. No. 5,511,689, Frank, and Japanese Utility Model Registration No. 2,126,815, Kanda, et al., each disclose a package for an adhesive-sided bandage including a bottom sheet and a top sheet, a release paper opposing the adhesive surface of the bandage and adhesive layers of different strengths on the top and bottom sheets and the bandage itself. The weakest adhesive allows the bottom sheet to be removed with the release paper to expose the adhesive side of the bandage while the bandage is adhered to the top sheet. The strongest adhesive is on the bandage so that it can be applied to the patient's skin for fast holding. An adhesive of intermediate strength holds the top sheet to the top of the entire bandage and gives way to allow removal of the top sheet therefrom after the bandage is secured to the patient's skin.

Neither the Frank package nor the Kanda, et al. package is believed to have been commercialized. Although the package of Frank, and possibly that of Kanda, et al., allows a one-handed application of the bandage to the patient and removal of the top sheet of the package, as shown in FIG. 3 of the Frank patent, there are problems in consistently obtaining the relative adhesive strengths and with having an adhesive layer on the top sheet of the package at the time of application to the patient. Having the relative adhesive strengths in the various relationships as described above is important to permit the package to work properly in the application of the bandage. In addition, it is necessary to have the top sheet adhere to the bottom sheet when the package is stored as well as sterilized, necessitating that the adhesive area is larger than the area of the bandage. In their respective applications, Frank and Kanda, et al. use only one adhesive to not only bond the top sheet to the bandage, but also to bond the top sheet to the bottom sheet to seal the package. In this application, the top and bottom sheets need to peel apart easily while also to stick together firmly enough to seal the package for sterilization purposes. With only one adhesive bonding the top sheet to the top surface of the bandage, this would not be possible. Furthermore, when the bandage and top sheet are pressed onto the skin, the adhesive on the top sheet adheres to the skin and hairs and blemishes thereon. When the top sheet of the package is subsequently removed, the hairs are pulled and the skin imperfections are irritated.

Therefore, it is a feature of the invention to provide a package comprising separable top and bottom layers adhered to each other for enclosing an adhesive bandage or the like, that allows one-handed application of the bandage with its separated top layer being used as the applicator. The applicator is void of any adhesive material that would come in contact with the skin, so when the bandage is applied, the only adhesive that comes in contact with the skin is the adhesive on the bandage itself.

It is another feature of the invention to provide a package comprising separable top and bottom layers adhered to each other for enclosing an adhesive bandage or the like, that allows the bottom layer to be removed from the top layer and allows the top layer to pop up from the bandage when the bandage is applied to the skin for ease of removal of the top layer.

SUMMARY OF THE INVENTION

The invention pertains to a more convenient and easy-to-use package for enclosing an adhesive-sided article, such as an adhesive bandage so that the adhesive-sided article can be removed from its package and placed on a target area using only a single hand while keeping the article free from contamination. Maintaining the sterile integrity of the article is particularly important for a medical bandage application. The sterile or other article is packaged between two cover sheets, a backing layer and a support layer, that are bonded together; the article is attached at one end to the top cover sheet or support layer. To dispense the article, the user pulls on a tab attached to the top cover sheet. The top cover sheet and the article peel away from the bottom sheet or backing layer, leaving the article in the user's hand with its adhesive exposed. The user may then apply the article directly to a target surface with the same hand and without shifting his grip on the tab. The top cover sheet comes away, or "pops up" from the article except at the single point of attachment, preventing the user from wrapping the article over the top cover sheet and permitting easy removal of the top cover sheet from the back of the article.

To permit the above application of the enclosed adhesive-sided article, the enclosing package includes facing bottom backing and top support sheets larger than the article, the opposing faces disposed with cohesive, at least peripheral to the article. A release layer having a non-sticking surface facing the adhesive side of the article is adhered to the backing layer. A small adhesive layer attaches one end of the non-adhesive side of the article to the support sheet.

A suitable "match book" dispenser secures packaged articles for ease of storage.

BRIEF DESCRIPTION OF THE DRAWINGS

So that the manner in which the above-recited features, advantages and objects of the invention, as well as others which will become apparent, are attained and can be understood in detail, more particular description of the invention briefly summarized above may be had by reference to the embodiments thereof which are illustrated in the drawings, which drawings form a part of this specification. It is to be noted, however, that the appended drawings illustrate only preferred embodiments of the invention and are therefore not to be considered limiting of its scope as the invention may admit to other equally effective embodiments.

In the drawings.

DETAILED DESCRIPTION OF THE PREFERRED EMBODIMENTS

Illustrative preferred embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention is directed to the problem of dispensing and preferably affixing with one hand an adhesive-sided article such as a label strip of tape, a therapeutic patch, an adhesive bandage or a decal. Specifically, the invention disclosed herein improves upon known methods of wrapping, unwrapping and dispensing such articles, many of which require the use of cumbersome, complex, and expensive dispensers. Because such dispensers are costly and take up a great deal of space, there are many locations that cannot be supplied with a dispenser for these articles even though it would be useful to provide one. The present invention, by way of distinction, includes practical embodiments that can easily be implemented in a space scarcely wider than the article being dispensed (less than two or three inches wide at suitable locations) and at extremely low cost. Indeed, as will be explained in more detail below, it is possible to implement the invention in a form that eliminates the dispenser entirely and thus consists exclusively of consumable and-disposable components.

Figure 1:
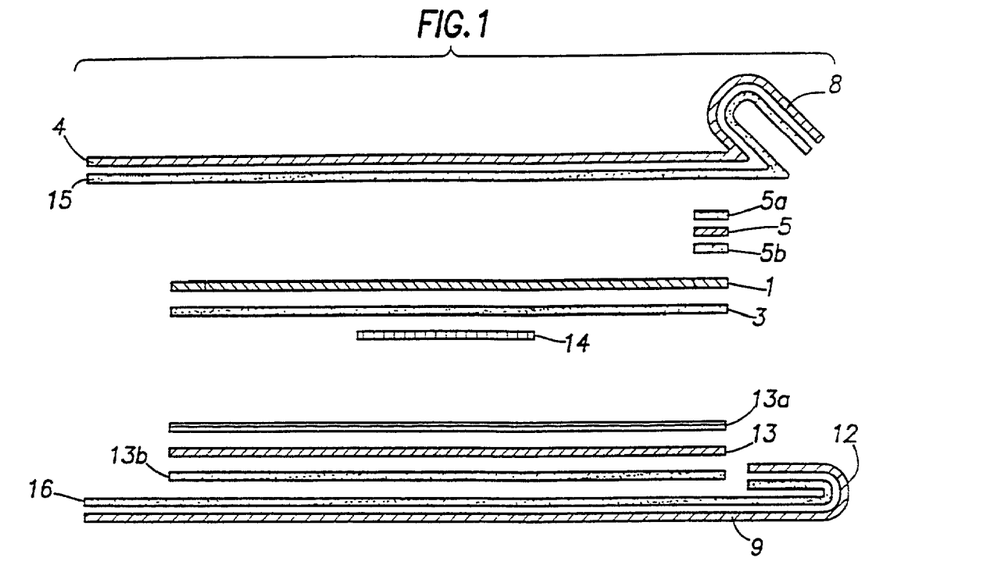
FIG. 1 depicts a graphically expanded cross-sectional view of the assembled article taken along the length of the article immediately before the top and bottom cover sheets or layers are sealed together.
Figure 2:
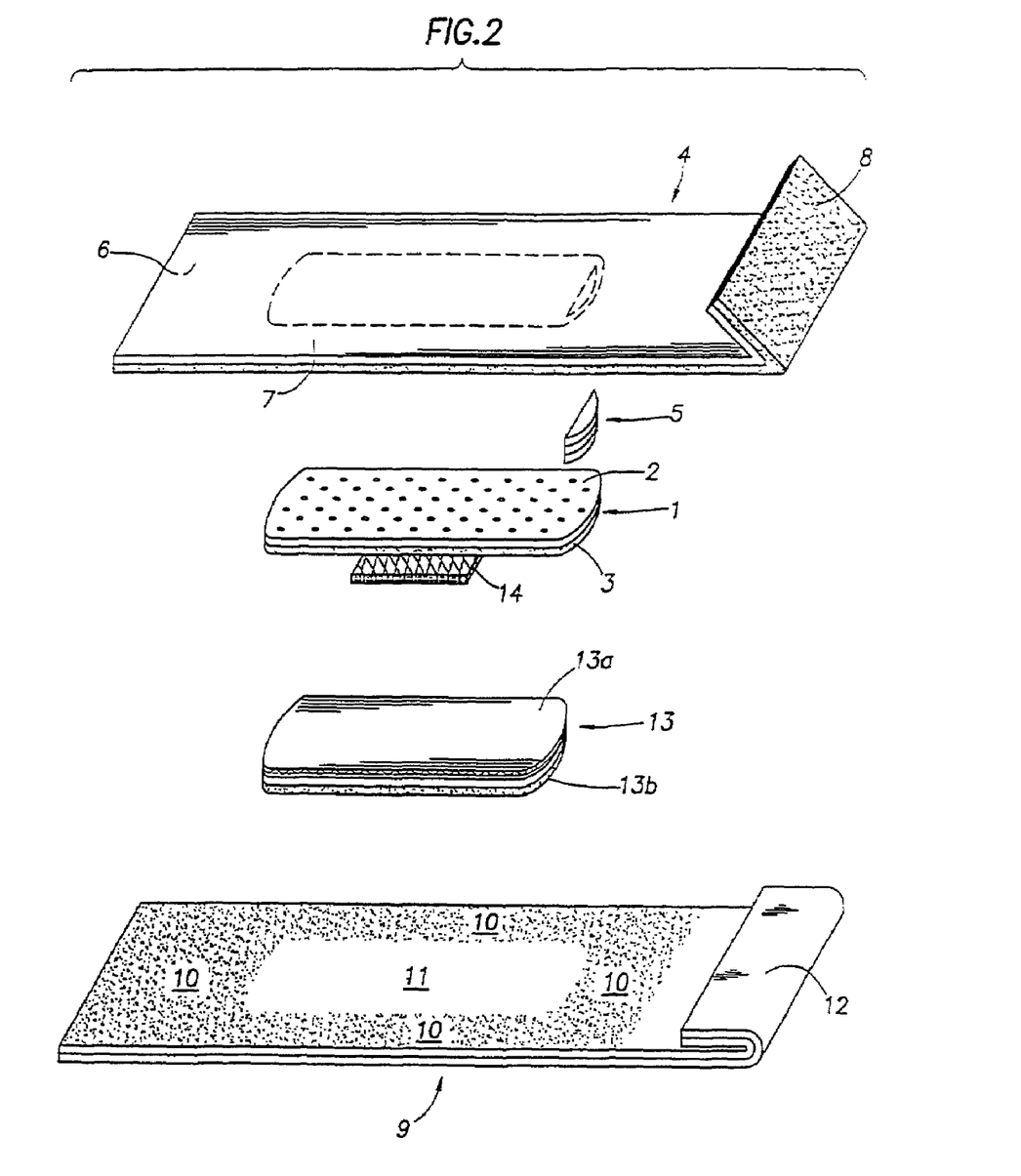
FIG. 2 shows an exploded view of a packaged adhesive-sided article in accordance with the present invention.

FIG. 1 depicts an article packaged in accordance with the present invention. An adhesive-sided article is made up of a backing sheet (1) with a first adhesive (3) disposed on one surface. Typically, the backing sheet for the article includes breathing holes, as shown. In this embodiment, the article is an adhesive bandage: a gauze pad (14) is secured by the adhesive to the backing sheet. The pad may be treated with a biochemically active compound, if desired. Nicotine, for example, may be applied to the pad or saturating the pad for use as a nicotine patch. Nitroglycerine pads are also available for heart patients. It will be apparent, however, that the particular nature or function of the article itself is not an essential component of the present invention, and that other useful articles ranging from medicated patches to decorative decals with appropriate printing and/or colorations may be identically packaged and applied. It. will also be apparent that although FIG. 1 and the other figures depict a generally rectangular article, the principles underlying the present invention are general and articles of nearly any size or shape may be packaged and applied using the technique described herein. Furthermore, the backing sheet may be made of any material appropriate for the task to be performed by the article. Materials such as paper, plastic, fabric, metal foils or layered combinations of the above are well known in tape and bandage applications, but the technique disclosed herein will also work with less flexible articles.

The adhesive-sided article is temporarily applied to a release layer (13) that has a facing area that is at least as large as the adhesive side of the article. Release layer (13) is firmly attached to a central region (11) of the bottom cover sheet (9) or backing layer by either an adhesive or cohesive (13b). This release layer also may consist of a coating applied to all or part of the cover sheet itself. Such an embodiment simplifies manufacturing, reduces the overall package thickness and eliminates paper which in turn eliminates waste material. In another embodiment, the release layer may comprise a separate piece of suitable material (13, 13a, 13b) that is attached to the cover sheet at some point during manufacture of the finished product. One material that works well as the release layer is paper coated with silicone (13a) on the side facing the article. A paper strip with an appropriate cohesive for use as a release layer is available from Emtech of Medina, Ohio.

The bottom cover sheet is longer and/or wider than adhesive-sided article (1). This excess length and/or width forms edge regions (10) on the cover sheet bordering the article. Where it is necessary or desirable to maintain the article in a sterile condition, it is thus possible to provide a releasable hermetic seal peripherally around the article by sealing all of the edges (6, 7) of the top cover sheet support layer (4) to the edges (10) of the bottom cover sheet. Additional excess length of the bottom cover sheet may also be provided at one end as an anchoring or tab region (12) that may be used to hold the bottom cover sheet fixed during application of the article or (as described in more detail below and shown in FIG. 6) as a location at which a fastener can hold a stack of the packaged articles together without interfering with their sealed compartments.

The article is covered from above by a top cover or support sheet (4) that also functions as the applicator of the article. The top cover sheet may be made of any convenient packaging material such as paper or plastic. In particular, the top cover sheet may be made of a transparent or translucent material in order to facilitate accurate placement of the article if such accuracy is important. This might be useful, for example, where the article is a bandage or surgical tape to be applied to a cut or incision, or where the article is one of several to be applied in close alignment on a common surface, such as letter or numeral decals on a mailbox.

The top cover sheet is longer and/or wider than the article, as is the bottom cover sheet, in order to provide end edge regions (6) or side edge regions (7) (or both) for sealing the top cover sheet to the bottom cover sheet around the article. Where there is no particular need for a sterile closure around the article, it is not necessary to provide all of the edge regions of the top and bottom cover sheets. For example, one could eliminate the side edge regions of both cover sheets, leaving a package held together at its ends by first adhesive (3), second adhesive (5), and the seal formed at the end edge region (6) farthest from the second adhesive. Similarly, it would be possible to eliminate the end edge region farthest from the tab (8), leaving the package held together by bonds in the side edge regions (7).

The top and bottom cover sheets are preferably secured together by treating each with a nonadhesive bonding material (a "cohesive") that adheres only to other surfaces coated with the same material, but does not adhere to untreated surfaces such as the backing sheet. This choice facilitates assembly of the packaged article because it allows the entire inside surface of the top and bottom cover sheets to be coated with cohesive without concern that the adhesive-sided article might adhere to the top cover sheet. Thus, layer (15) is disposed on the bottom of sheet (4) and layer (16) is disposed on the top of sheet (9). To accomplish the same objective with an adhesive bonding material would require precise application of the adhesive along only the edges of the cover sheets. The application of too much adhesive would cause the article to adhere too strongly to the top cover sheet; use of too little would tend to result in gaps in the closure that would render the package unsuitable for sterile applications. Paper having a suitable cohesive attached thereto and separate cohesive material is available from Bonarko located in Plymouth, Ind. A suitable cohesive material is available from A. T. O. Findley and is known as Cold Seal.

The lengthwise end (2) of the article (that is, an end of the article along its longest dimension) closest to the anchoring region (12) of the bottom cover sheet is releasably attached to the top cover sheet by a narrow strip of a second adhesive component (5). Anchoring region or tab (12) is created by folding the extended end of sheet (9) over on itself so that two cohesive surfaces face and adhere to each other. This adhesive component is selected so that the article will adhere to the top cover sheet (4) when the top and bottom cover sheets are separated, and also so that the top cover sheet will detach easily from the article once the article is delivered and affixed to a target surface. One method for achieving this selectivity is to employ a small piece of backing material such as cellophane coated with two adhesives (5a) and (5b) of different tack, one on each side. Adhesive materials (5a) and (5b) on double-sided backing (5) are preferably about as strong as adhesive material (3) on adhesive-sided article (1). Preferably, the bond can be even a little stronger since the area of tape or layer (5) is small relative to the area of the adhesive side of article (1) that is to be placed on the receiving surface of the patient or other target surface. When the top support sheet is removed from the adhesive-sided article, it is grasped at the end that has popped up or that is not adhered to the article and pulled lengthwise, not straight up. Thus, layer (5a) releases from article (1) without causing the adhesive of article (1) to pull-away from the receiving surface.

The two adhesives (5a) and (5b) can be selected so that the stronger adhesive faces the top cover sheet to ensure that when the top cover sheet is removed, the second adhesive component will be removed with it rather than adhering to the backing sheet. In other words, adhesive layer (5a) is preferably stronger than adhesive layer (5b). A source for such tape with appropriate adhesive layers is Tapes & Tech Solutions located in Nashville, Tennessee. Although the area of component (5) is illustrated as being relatively small with respect to the area of the article, it may be quite large. Alternatively, component (5) can be a glue or other adhesive applied directly to the area occupied in the illustration by the backing material just described for component (5).

A pull tab (8) is formed by extending a segment of the top cover sheet beyond the previously described end edge region (6) at the same end of the article at which the top sheet is attached by the second adhesive (5) and at which the anchoring region (12) extends from the bottom cover sheet. The tab is folded under or toward the article and away from the anchoring region so that the top cover sheet may be peeled away from the bottom cover sheet by pulling on the tab while the anchoring region or tab (12) is held stationary. Because the facing portions of the sheet forming the tab are both disposed with cohesive, the two portions seal on each other. It will be apparent that the tab (8), the second adhesive (5) and the anchoring region (12) must all be located at the same end of the article in order for this peeling action to detach the article from the release layer (13) of the bottom cover sheet while keeping the article attached to the top cover sheet. It is possible, however, to locate the anchoring region adjoining the side edge (7) instead of the end edge (6) as long as the anchoring region at least adjoins that portion of the side edge next to the end edge beyond the second adhesive (5). In particular, one could assemble a number of articles into a coiled roll with the tabs of the top cover sheets at the sides of the coil, so that an article is dispensed by pulling the article's tab across the width of the roll rather than along its length.

Figure 6:
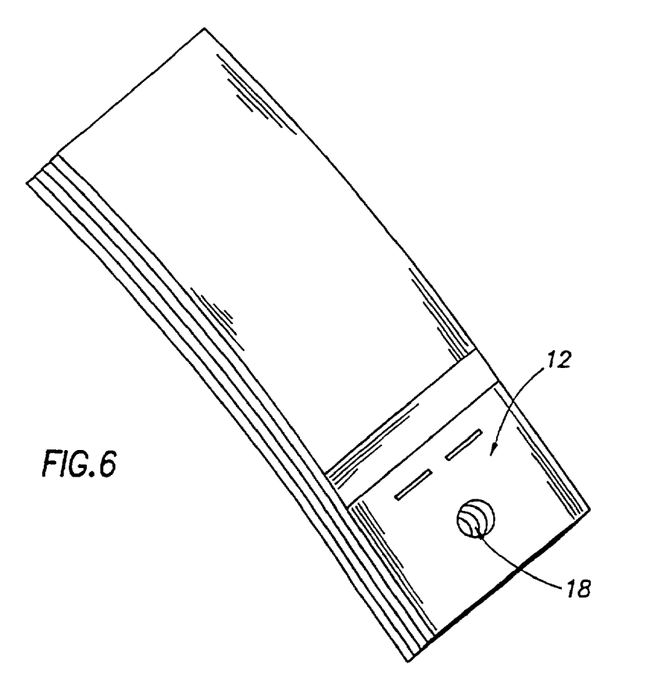
FIG. 6 depicts an assemblage of several of the articles of the present invention into a matchbook-like dispenser.
Figure 8:
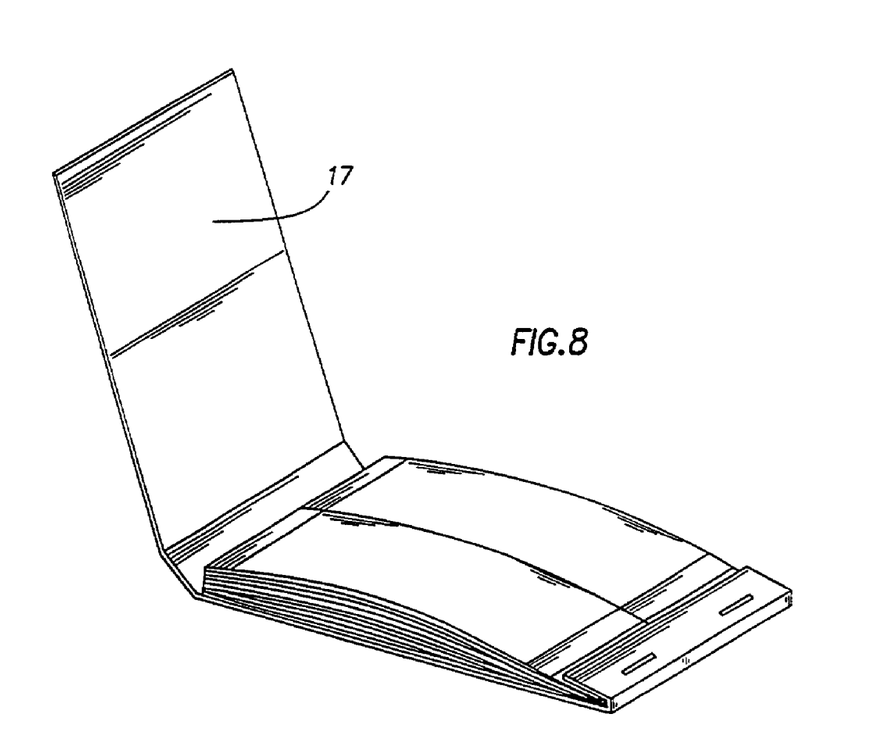
FIG. 8 depicts the same assemblage as FIG. 7 with the protective cover opened to dispense the articles.
Figure 9:
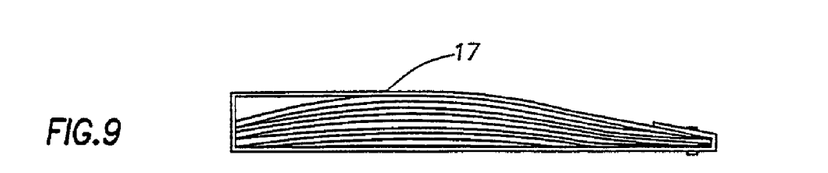
FIG. 9 depicts a side-edge view of the same assemblage as FIGS. 7 and 8.

Although FIG. 1 is expanded and exaggerated for illustration purposes, it will be apparent that FIG. 1 depicts a longitudinal cross-section of the adhesive-sided article and its packaging, just before the top and bottom cover sheets are sealed together. In making up the package, one could also provide a second release surface on the side of the top cover sheet facing away from the second adhesive. Of course, it would have some affinity to bond with adhesive layer (5). This modification would permit one to construct a stack of articles separated by single intermediate cover sheets, each article's bottom cover sheet serving also as the top cover sheet/applicator for the article immediately below it in the stack. In this stacked formation, as best illustrated in FIGS. 6 and 8, by utilizing the upper surface of a top cover sheet of an article as the bottom cover sheet for a successive article, the amount of packaging required for the overall assembly is reduced by approximately one-half, thereby simplifying manufacture of the packaging and reducing the amount of paper required for packaging.

Figure 3:
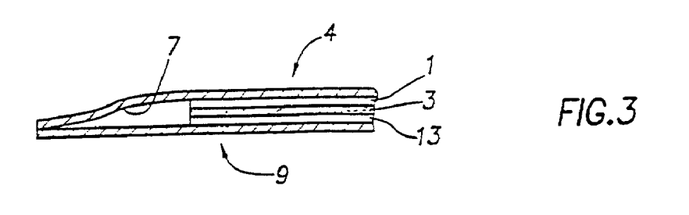
FIG. 3 depicts a cross-sectional view of the assembled article taken along the width of the article after the top and bottom cover sheets are sealed together.

FIG. 3 depicts a partial cross-section of the same article through its width, taken just after the cover sheets are sealed together.

Figure 4:
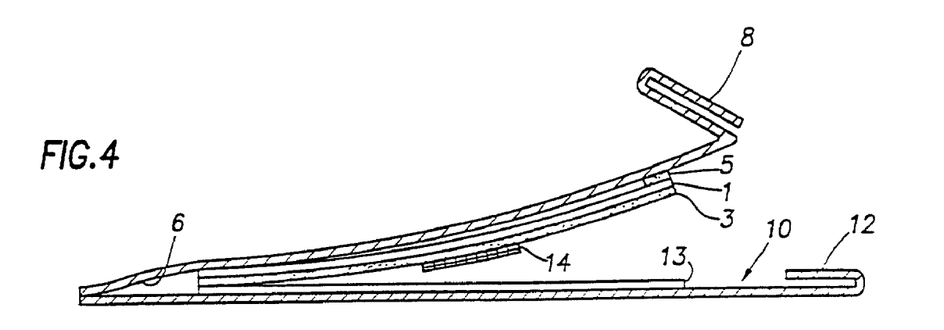
FIG. 4 depicts the method of removing the article from the bottom or backing sheet by pulling on the tab of the top or support sheet.

FIG. 4 depicts the first step in applying the article. By pulling tab (8) away from the bottom cover sheet and away from anchoring region (12), the user simultaneously removes the article from its packaging and exposes its adhesive (3) for application to the target surface. The second adhesive or layer (5) secures one end of the article to the top cover sheet during this operation.

Figure 5:
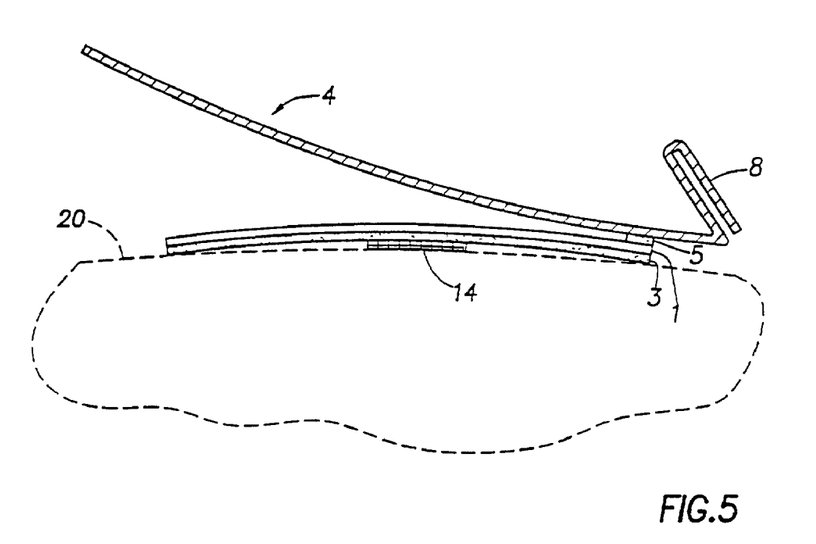
FIG. 5 depicts the application of the article to a target surface showing self-releasing or pop-up feature.

In FIG. 5, the article is delivered to target surface (20). The top cover sheet (4) is attached to the article only by a small amount of adhesive material (5) at the top surface of the article's lengthwise end (2), as previously discussed. The cover sheet may thus be easily detached from the article once the article is fixed to the target surface by its adhesive (3). In addition, the action of applying the article tends to cause the top cover sheet to "self-release" or "pop up"—that is, to curl upward and away from the article, further facilitating removal of the top cover sheet. This self-release action is particularly important where the article is to be applied to a small cylindrical surface (such as bandaging a finger or labeling a wire or pipe) because this mechanism prevents the user from wrapping the article's back over the top cover sheet, which would make the cover sheet extremely difficult to detach. It will be appreciated that the present invention obviates any need for the user to change his grip on the top cover sheet during application of the article. This tends to reduce the likelihood that the article will fold and adhere to itself in a way that might complicate application. In addition, the ability to apply the article without altering one's grip would allow a user to secure the article easily to a point beyond his normal reach by using a surgical clamp, needle-nose pliers or the like to grasp the tab of the top cover sheet throughout the operation. In the case of bandages and other medical articles, a significant opportunity for contamination of the sterile surface is also eliminated. Finally, the present invention eliminates any need for the user to touch the adhesive on the backing sheet. This further facilitates application and makes it possible, for example, to dispense and apply the article while the user is wearing latex or other rubber gloves.

FIG. 6 depicts a stack of the packaged articles assembled to form a convenient dispenser. In the figure, the articles are simply stapled together through the anchoring regions (12) of each bottom cover sheet (9); but numerous other known methods of fastening several articles together at their anchoring regions, such as applying adhesive to the faces or edges of these regions or simply mechanically clamping the articles with a binder clip, may be employed without departing from the scope of this disclosure. By adding a mounting hole (18), it becomes possible to hang the assembly from a spindle, nail, hook, or other projection at a dispensing station. When the assembly is thus suspended, true one-handed dispensing and application of the articles becomes possible because the anchoring region of each article's bottom cover sheet is held in place by the hanging hardware. This embodiment of the invention might be especially useful in hospitals, where the need for bandages is frequent and IV stands are readily available; but it will be apparent that similar assemblies may be used in any location where it is desirable to have several adhesive-sided articles readily available for application. It should also be apparent that this embodiment effectively obviates any need for a permanent dispenser, since the dispensing assembly consists of only the articles themselves, their consumable or disposable packaging materials, and one or more inexpensive fasteners.

Figure 7:
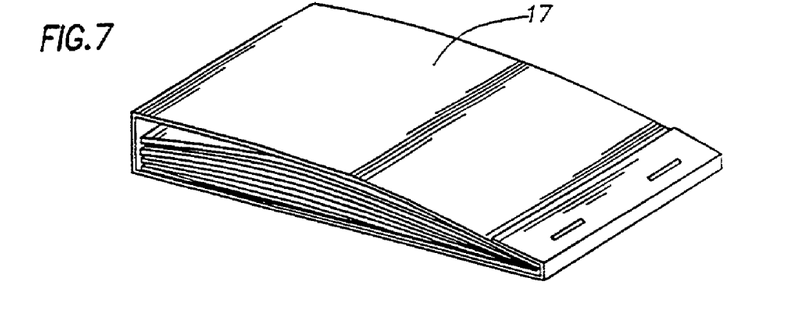
FIG. 7 depicts a similar assemblage with a protective cover to prevent crushing.

It may be desirable, however to provide the assembly with a folded reclosable cover (17), as shown more clearly in FIGS. 7 and 8, to protect the articles from crushing or contamination, and to make the assembly convenient to carry in a pocket. The addition of a cover provides additional options for mounting the assembly at a dispensing point, such as the application of double-sided adhesive to the back of the cover or the attachment of a hanging loop or similar device at the end of the assembly where the articles are fastened together.

The process for manufacturing the packaged adhesive-sided articles of the present invention proceeds in two sets of steps. The first set of operations prepares each of the five or six components of the packaged article (top and bottom cover strips, release layer or liner, backing sheet with first adhesive, second adhesive, and optionally a pad) for assembly into the finished product. These steps may be carried out simultaneously or sequentially and in any order. The top and bottom cover sheets are prepared for assembly by coating one side of each with the cohesive material described above. The backing material of the article itself is coated with adhesive on one side and, for ease in handling, is backed with a temporary release paper that is not part of the finished product. This backing material may also be perforated with breathing holes at this point. The release liner is coated first with a silicone on one side, then with adhesive or cohesive on the other side. All four of these components, and the pad if one is to be applied, are typically furnished in continuous rolls far wider than the process requires and must therefore be cut to appropriate widths before assembly. After cutting, a nonstick tab is formed on one edge of each cover sheet by folding the edge over on itself so that the cohesive material contacts itself. The second adhesive is performed by applying two adhesive layers to opposite sides of a substrate as described above.

The second set of operations assembles the prepared components into the finished packaged product. Although the process is best carried out by using continuous production machinery, it may also be performed batchwise from appropriate starting materials without altering the function of the completed product. The backing sheet is separated from its temporary release paper and the pad material is mounted on the first adhesive. The silicone-coated face of the release liner is applied to the first adhesive over the pad, leaving the adhesive-coated or cohesive-coated side exposed. The second adhesive is applied to a precise location on the back of the backing sheet (that is, the side not treated with the first adhesive), and the entire assembly is die-cut to produce articles of the desired shape and size, such that the location where the second adhesive was applied becomes the end of the article.

Finally, the top and bottom cover sheets are applied with pressure. This operation forms a seal of cohesive material around the article, attaches the release liner to the bottom cover sheet, and secures the top cover sheet to the second adhesive on the end of the backing sheet. The resulting assembly consists of a continuous sheet of packaged articles that may be separated into individual packages or perforated to permit such separation later.

Numerous minor variations in the order of the manufacturing steps may be made without affecting the quality or function of the resulting product, but it is essential for proper operability of the finished product that the second adhesive not extend beyond the backing sheet onto the bottom cover sheet.

It will be apparent to one of ordinary skill in the art that many changes or modifications may be made to the invention described above without departing from the spirit or scope of the appended claims.

What is claimed is:

1. A packaged article for one-handed application, comprising
    an adhesive-sided article having top and bottom surfaces and an adhesive disposed on at least a portion of said bottom surface,
    a bottom backing sheet having a top surface larger than said adhesive-sided article and a cohesive disposed on said top surface,
    a release layer at least as large as the adhesive of said adhesive-sided article, said release layer comprising a non-sticking substance disposed on said top surface of said bottom backing sheet,
    a top support sheet having a bottom surface larger than said adhesive-sided article and a cohesive disposed on said bottom surface,
    an adhesive layer for attaching to a portion of one end of said top surface of said adhesive-sided article and to a portion of said bottom surface of said top support sheet,
    said bottom surface of said top support sheet enclosing said adhesive-sided article by adhering to that portion of said bottom backing sheet that is larger than said release layer so that said bottom backing sheet and release layer are removed together to expose said bottom surface of said adhesive-sided article for application to a receiving surface after which said top support sheet is removed from said adhesive-sided article.

2. A packaged article in accordance with claim 1, wherein said non-sticking substance of said release layer is silicone.

3. A packaged article in accordance with claim 1, wherein said release layer is centrally disposed on said bottom backing sheet.

4. A packaged article in accordance with claim 1, wherein said adhesive-sided article is a bandage having a bandage backing and a sterile pad adhesively attached to a portion thereof.

5. The packaged article in accordance with claim 4, further comprising a biochemically active material.

6. The packaged article in accordance with claim 5, wherein said biochemically active material is disposed within said pad.

7. The packaged article in accordance with claim 5, wherein said biochemically active material is disposed in said pad.

8. The packaged article in accordance with claim 5, wherein said biochemically active material is nicotine.

9. The packaged article in accordance with claim 5, wherein said biochemically active material is nitroglycerine.

10. A packaged article in accordance with claim 1, wherein said adhesive layer is a double-sided tape having top and bottom surfaces and adhesive disposed on both said top surface and on said bottom surface.

11. A packaged article in accordance with claim 10, wherein the adhesive of said adhesive layer with the bottom surface of said top support is stronger than the adhesive of said adhesive layer with the top surface of said adhesive-sided article.

12. A packaged article in accordance with claim 1, wherein said adhesive layer has a stronger bond with said top support sheet than the bond between said adhesive-sided article and said release layer.

13. The packaged article of claim 1 wherein at least a portion of said adhesive-sided article is transparent.

14. The packaged article of claim 1 wherein at least a portion of said adhesive-sided article is translucent.

15. A packaged article in accordance with claim 1, wherein said cohesive is a bonding material that permits said bottom backing sheet and said top support sheet to be releasably attached to one another.

16. A packaged article in accordance with claim 15, wherein said bonding material is non-adhesive.

17. A packaged article in accordance with claim 15, wherein said bonding material need only be applied to either said bottom backing sheet or said top support sheet in order to permit said bottom backing sheet and aid top support sheet to be releasably attached ton one another.

18. A packaged article for one-handed application, comprising:
    first and second adhesive-sided articles, each having top and bottom surfaces and an adhesive disposed on at least a portion of said bottom surface,
    a first backing sheet having a top surface and a bottom surface, wherein each of said surfaces is larger than said adhesive-sided articles and each of said surfaces is provided with a cohesive disposed thereon,
    a first release layer at least as large as the adhesive of said adhesive-sided articles, said first release layer comprising a non-sticking substances and said first release layer disposed on said top surface of said first backing sheet;
    a second backing sheet having a top surface and a bottom surface, wherein said bottom surface is larger than said adhesive-sided articles and said bottom surface is provided with a cohesive disposed thereon,
    a first adhesive layer for attaching to a portion of one end of said top surface of said first adhesive-sided article to a portion of said bottom surface of said second backing sheet,
    a third backing sheet having a top surface and a bottom surface, wherein said top surface is larger than adhesive-sided articles and said top surface is provided with a cohesive disposed thereon,
    a second release layer at least as large as the adhesive of said adhesive-sided articles said second release layer comprising a non-sticking substance and said second release layer disposed on said top surface of said third backing sheet,
    a second adhesive layer for attaching to a portion of one end of said top surface of said second adhesive-sided article to a portion of said bottom surface of said first backing sheet,
    wherein said bottom surface of said second backing sheet encloses said first adhesive-sided article by adhering to the top surface of said first backing sheet that is larger than said first release layer and wherein said bottom surface of said first backing sheet encloses said second adhesive-sided article by adhering to the top surface of said third backing sheet that is larger than said second release layer, such that separation of a backing sheet and release layer together form the bottom of the backing sheet to which they are attached exposes said bottom surface of an adhesive-sided article for application to a receiving surface, after which the bottom of the backing sheet carrying the exposed adhesive-sided article is removed from said adhesive sided article.

19. A packaged article in accordance with claim 18, further comprising a plurality of backing sheets and adhesive-sided articles, wherein said backing sheets are attached to one another in a stacked relationship and an adhesive-sided article is disposed between adjacent backing sheets.

20. A packaged article in accordance with claim 18, further comprising:
  a plurality of said packaged adhesive-sided articles, wherein said support sheets for said packaged articles includes an extension tab and an extended anchoring portion; and
  a fastener securing said anchoring portions of said backing sheets together, wherein said fastener does not secure said extension tabs.

21. A packaged article in accordance with claim 20, further comprising a reclosable cover at least partially enclosing said packaged articles, wherein said fastener secures said reclosable cover to said extended anchoring portions of said backing sheets.

22. The packaged article in accordance with claim 18, wherein at lease one of said release layers further comprises a release sheet, wherein said non-sticking substance is disposed on said release sheet which is adhered to said top surface of said backing sheet.

23. The packaged article in accordance with claim 18, wherein said non-sticking substance of at lease one of said release layers is applied directly to said backing sheet.

24. The packaged article in accordance with claim 18, wherein said non-sticking substance is silicone.

25. The packaged article in accordance with claim 18, wherein said adhesive-sided article is a bandage having a bandage backing and a sterile pad adhesively attached to a portion thereof.

26. The packaged article in accordance with claim 25, further comprising a biochemically active material.

27. The packaged article in accordance with claim 26, wherein said biochemically active material is disposed within said pad.

28. The packaged article in accordance with claim 26, wherein said biochemically active material is disposed on said pad.

29. The packaged article in accordance with claim 26, wherein said biochemically active material is nicotine.

30. The packaged article in accordance with claim 26, wherein said biochemically active material is nitroglycerine.

31. A packaged article in accordance with claim 18, wherein said adhesive layer is a double-sided tape having top and bottom surfaces and adhesive disposed on both said to surface and on said bottom surface.

32. A packaged article in accordance with claim 31, wherein the, adhesive of said adhesive layer with the bottom surface of said top support sheet is stronger than the adhesive of said adhesive layer with the top surface of said adhesive-sided article.

33. A packaged article in accordance with claim 18, wherein said adhesive layer has a stronger bond with said top support sheet than the bond between said adhesive-sided article and said release layer.

34. The packaged article of claim 18 wherein at least a portion of said adhesive-sided article is transparent.

35. The packaged article of claim 18 wherein at least a portion of said adhesive-sided article is translucent.

36. A packaged article in accordance with claim 18, wherein said cohesive is a bonding material that permits said backing sheets to be releasably attached to one another.

37. A packaged article in accordance with claim 36, wherein said bonding material is non-adhesive.

38. A packaged article in accordance with claim 36, wherein said bonding material need only be applied to one surface of a backing sheet in order to permit adjacent backing sheets to be releasably attached to one another.

* * * * *